United States Patent [19]

Lindholm-Ventola

[11] Patent Number: 5,540,670
[45] Date of Patent: Jul. 30, 1996

[54] APPARATUS FOR COLLECTING SEMEN

[76] Inventor: Jukka Lindholm-Ventola, Melliläntie 760, FIN-32200 Loimaa, Finland

[21] Appl. No.: 302,835

[22] PCT Filed: Mar. 19, 1993

[86] PCT No.: PCT/FI93/00100

§ 371 Date: Oct. 18, 1994

§ 102(e) Date: Oct. 18, 1994

[87] PCT Pub. No.: WO93/18730

PCT Pub. Date: Sep. 30, 1993

[30] Foreign Application Priority Data

Mar. 19, 1992 [FI] Finland .................................. 921189

[51] Int. Cl.$^6$ ...................................................... A61F 5/44
[52] U.S. Cl. .......................... 604/349; 604/317; 128/762
[58] Field of Search .............................. 119/95; 128/760, 128/762; 604/317, 349; 73/864.51, 863.52, 219

[56] References Cited

U.S. PATENT DOCUMENTS

| | | |
|---|---|---|
| 2,603,442 | 7/1951 | Snyder . |
| 2,792,836 | 5/1957 | Reynolds, Jr. et al. ................. 604/317 |
| 3,547,102 | 12/1970 | Frenkel et al. ........................... 604/317 |
| 3,992,913 | 12/1975 | Scott .......................................... 73/219 |
| 4,230,195 | 10/1980 | Graffin ........................................ 177/1 |
| 4,407,379 | 10/1983 | Pryor et al. ............................... 177/52 |
| 4,718,288 | 1/1988 | Leschonski et al. ...................... 73/863 |
| 4,805,462 | 2/1989 | Lobschies ............................. 73/861.36 |
| 5,059,310 | 10/1991 | Fischer et al. ........................... 209/237 |
| 5,218,971 | 6/1993 | Minami et al. .......................... 128/760 |

FOREIGN PATENT DOCUMENTS

| | | |
|---|---|---|
| 342399 | 5/1978 | U.S.S.R. . |
| 923545 | 5/1982 | U.S.S.R. . |
| 1017321 | 5/1983 | U.S.S.R. . |
| 1120993 | 10/1984 | U.S.S.R. . |

*Primary Examiner*—David H. Willse
*Assistant Examiner*—Mark O. Polluta
*Attorney, Agent, or Firm*—Nixon & Vanderhye

[57] ABSTRACT

An apparatus for collecting semen to be used in animal breeding by means of a collecting apparatus connected to an artificial vagina. In the collecting apparatus, a collector funnel is fitted between the artificial vagina and a receiver, where the funnel has an upper semen-receiving opening and a lower discharge opening. A holder outside the discharge opening of the funnel of the collecting apparatus positions at least one semen receiver below the discharge opening. To the holder of the collecting apparatus are fitted weighing elements for weighing the contents of the receiver outside the discharge opening of the collector funnel.

8 Claims, 3 Drawing Sheets

APPARATUS FOR COLLECTING SEMEN

FIELD OF THE INVENTION

The object of the invention is an apparatus for collecting semen to be used in animal breeding, by means of a collecting apparatus connected to an artificial vagina.

BACKGROUND OF THE INVENTION

Artificial insemination is used widely in modern animal breeding. Artificial insemination of horses and zoo animals has also increased considerably. Traditionally, for example in collecting semen to be used in horse breeding, two different methods have been used, the so-called open and closed methods.

When using the open method, one person is required to hold the stallion and another to hold the mare, and if there is no dummy horse available, yet another person is required to hold the artificial vagina and a further person, that is, a so-called semen collector, to hold the collector funnel. The collector carrying out the work must be experienced, because the stallion pushes strongly with its hind legs when serving, and hits and strikes the mare with its front hooves. Also the mare moves, which makes collecting the semen considerably more difficult. Collecting the semen must, therefore, be considered dangerous and difficult, and the safety of the assisting personnel cannot always be guaranteed. Furthermore, using a mare in heat, and its unpredictable behaviour when semen is collected, constitute a considerable risk to the stallion. The mare may kick the stallion breaking its leg, or otherwise injure the stallion.

In the closed method, the whole ejaculation is collected by means of a receiver or bag attached to the end of the artificial vagina, whereas in the open method the aim is to collect those fractions of the ejaculation with the highest sperm density into a funnel and into the receiver, bag, or the like attached to it.

The stallion ejaculates in pulses. The first parts, or fractions, of the semen contain sperm and the rest only seminal plasm which comes from the different sexual glands. The stallion's penis, and particular its end, the glans, move during serving and ejaculation which makes successful collection of the semen difficult. The risk, therefore, exists that a part of the semen will not be caught in the funnel and a part splashes out of the funnel because the first valuable parts of the semen come out from the seminal duct under high pressure. It is fairly common that all the valuable parts of the ejaculation are not collected, and because of this, using the closed method is more common than using the open method.

Problems normally arise when the stallion pushes its penis several times through the artificial vagina before ejaculating. During this, impurities from the stallion's penis adhere to the lubricant in the interior of the vagina. Thus, in the closed system, the semen is partly contaminated by impurities as it flows from the vagina into the receiver. In the open method, on the other hand, it is possible to collect microbiologically and bacteriologically pure semen because there is no contamination between the semen and the vagina. The end of the penis and the seminal duct are outside the vagina as ejaculation takes place, and the semen is collected by catching the fractions in the funnel.

Another disadvantage of the closed method is that the unnecessary parts of the seminal plasm, which also reduce the preservation of the semen and its tolerance during deep-freezing, mix with the important parts of the ejaculation. At the initial stage of taking the semen, the parts of the seminal plasm cannot, therefore, be accurately separated. The seminal plasm can, however, be separated after collection by straining or centrifuging the semen. Due to the contamination in the vagina, the degree of purity of semen collected and treated in this way is not equivalent to that of semen collected by the open method. Straining and centrifuging also delay the further treatment of the semen, which is sensitive to air and light, which treatment should take place as soon as possible after collection.

If the busiest breeding season is underway and the stallion concerned is a valuable one from the point of view of breeding—for the semen of which there is a high demand—the open method involves several risk factors. Success is often dependent on the experience of the semen collector and on luck, and therefore in western countries a closed artificial vagina is generally used where valuable stallions are concerned.

The disadvantage of the above known methods is that from the collected semen the vital sperms needed in artificial insemination cannot immediately, at the initial stage, be accurately separated, but these are either lost or they mix with large amounts of semen useless for insemination. In addition, the safety of the assisting personnel and of the stallion cannot be guaranteed.

SUMMARY OF THE INVENTION

The aim of the present invention is to eliminate the foregoing problems and to achieve a new method and collecting apparatus which do not have the disadvantages described above.

It is characteristic of the method relating to the invention that semen is collected so that the semen released in the ejaculation is collected and sorted in stages into different containers.

It is characteristic of the apparatus relating to the invention that a collector funnel is fitted between the artificial vagina and the receiver, the said funnel comprising an upper semen-receiving opening and a lower discharge opening, directed mainly downwards, and under the discharge opening a holder for several receivers. The apparatus also comprises elements fitted to the holder for weighing the contents of the receiver under the discharge opening. For moving the holder of the element and the collector funnel with respect to each other on the basis of a signal given by the weighing elements, an empty receiver is moved under the discharge opening once the previous receiver has been filled.

By means of the present apparatus, the semen of the stallion is collected so that the ejaculated semen is sorted in stages into different containers. Thus, for the artificial insemination of mares the initial fraction of the ejaculation is used, which can be preserved longer in diluted form. Preliminary research results also show that with the initial fractions the pregnancy results are better than with the final fractions.

The collector funnel is attached to the frame of the apparatus, whereas the holder is a plate rotating around the shaft. The receivers can be fitted at a circumferential distance from each other, at a distance from the shaft determined by the collector funnel discharge opening, the said shaft being arranged so as to be operated by the drive unit acting as the transfer element.

The weighing elements consist of a measuring device reacting to the weight fitted in the holder under the receiver, the said device being electrically coupled to a transfer device, or the weighing elements are adjustable scales fitted to the holder and supporting the receiver, there being a sensor between that end of the scales which is on the side of the receiver, and the holder, the said sensor being electrically coupled to the transfer device.

By means of the invention, semen can be sorted more accurately than has been known previously. The quality and preserving properties of the semen also improve thanks to quick collection. However, fewer assisting personnel are required for collecting the semen and at the same time the safety of the assisting personnel and the serving stallion is improved.

BRIEF DESCRIPTION OF THE DRAWINGS

The invention is described with examples in the following, with reference to the appended drawings in which.

DETAILED DESCRIPTION OF THE DRAWINGS

Figure 1:
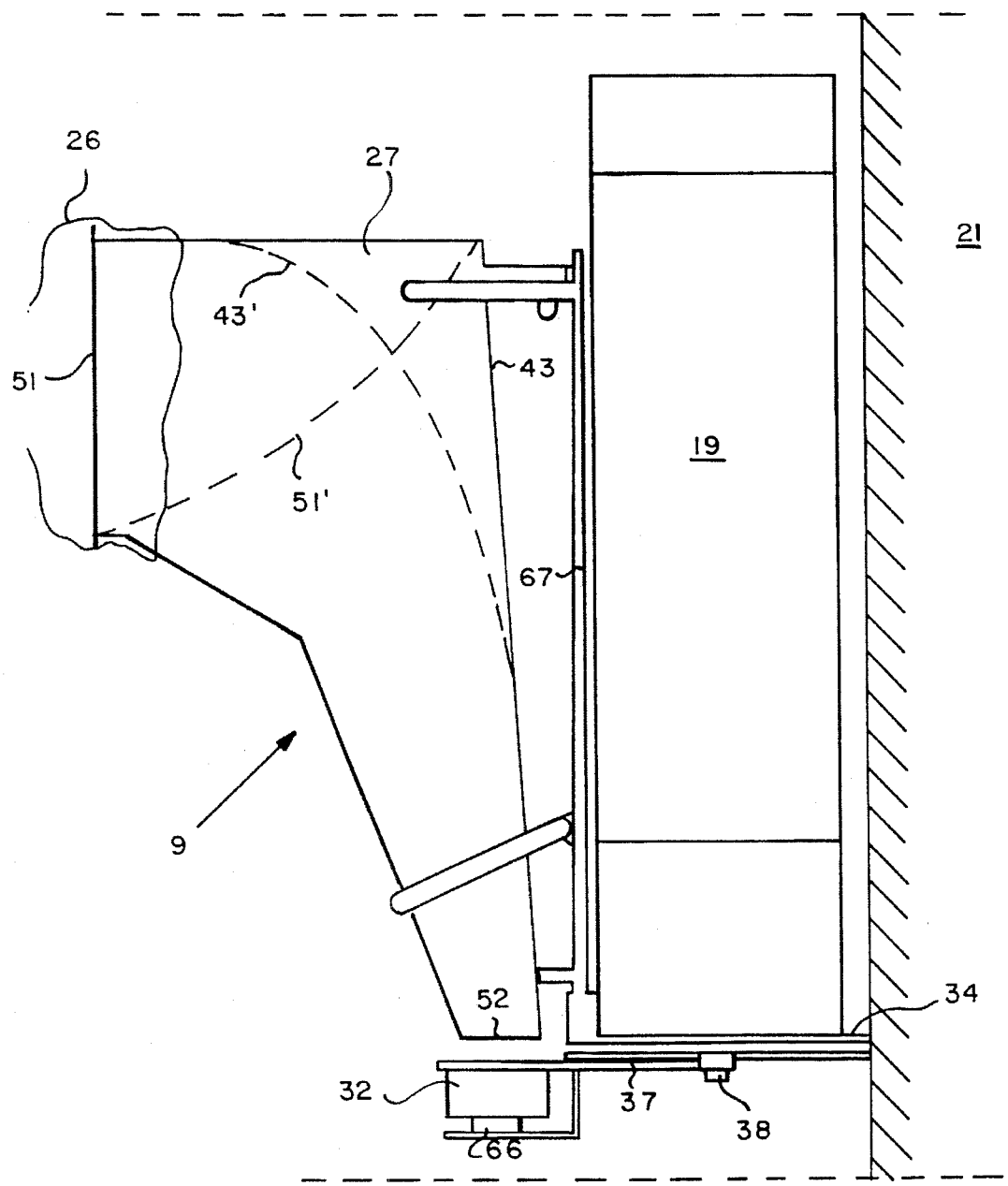
FIG. 1 shows a side view of the collecting apparatus relating to the invention.

FIG. 1 shows an apparatus for collecting horse semen. With the collecting apparatus 9 relating to the invention, semen is collected so that all the semen released in the ejaculation is collected in stages through the collector funnel 27, into separate receivers 32. Between the artificial vagina 12 (FIG. 3) and the receiver 32 is fitted a collector funnel 27, having an upper semen-receiving opening 51 and a lower discharge opening 52, directed mainly downwards. The shape of the receiving opening 51, 51' of the funnel 27 used in the collecting apparatus 9 may vary depending on the location and shape of the rear wall 43, 43' of the funnel used. The rear wall 43, 43' of the funnel 27 stops the movement of the semen and effects an even flow towards the discharge opening 52 of the funnel 27. Collection takes place automatically by means of an electrical drive unit 19 which is fastened by means of a fastening rack 34 and the extension of the dummy horse's supporting leg 21 to the frame. The weighing element 66, situated under the receiver 32 and reacting to weight, gives an impulse to the drive unit through an electrical control system, when the required amount of semen has collected in the receiver.

The drive unit 19 moves the holder plate 37 of the receiver. The holder plate 37 fastened to the shaft 38 turns just enough for the receiver 32 to move aside from under the funnel 27, and for the following cup-like receiver 32 to move under the funnel. The total duration of the ejaculation is only a few seconds, which means that the average time used for changing the receiver 32 is only some 0.5 s. The interior of the artificial vagina is protected with a disposable protective film 26, which is fastened by its other end to the funnel 27. By using the protective film 26, good external hygiene is also achieved. The funnel 27 is fastened to the funnel fastening rack 67, from which it can easily be removed for cleaning and sterilization.

Figure 2:
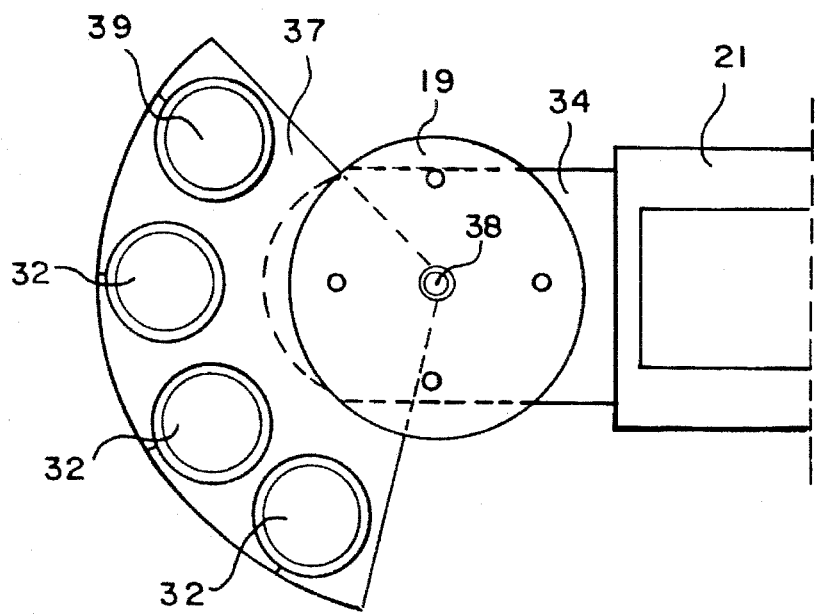
FIG. 2 shows the holder plate for the receivers of the semen collecting apparatus of FIG. 1, as seen from above.

FIG. 2 shows the holder plate 37 for the receivers of the semen collecting apparatus 9 of FIG. 1, as seen from above. All the semen released in the ejaculation is collected in stages into separate receivers 32 and 39. The holder plate 37 is moved automatically by means of the electrical drive unit 19, which is fastened to the frame by means of the fastening rack 34 and the extension of the supporting leg 21. The holder plate 37 is fastened by means of a shaft 38 to the drive unit 19. There are three receivers 32 in the holder plate 37, and a fourth receiver 39 acts as a precipitate cup, in order that proper separation is achieved. Precisely the desired amount, preferably 7 g, of semen is collected into the receivers 32, and the rest, that is, the semen unsuitable for artificial insemination, or the almost spermless parts of the seminal plasm are collected in the receiver 39. If necessary, the receiver 39 can be left without a measuring element reacting to the weight of the semen. The holder plate 37 turns just enough for the receiver 32 to move aside from under the funnel 27, and for the following cup 32 to move under the funnel.

Figure 3:
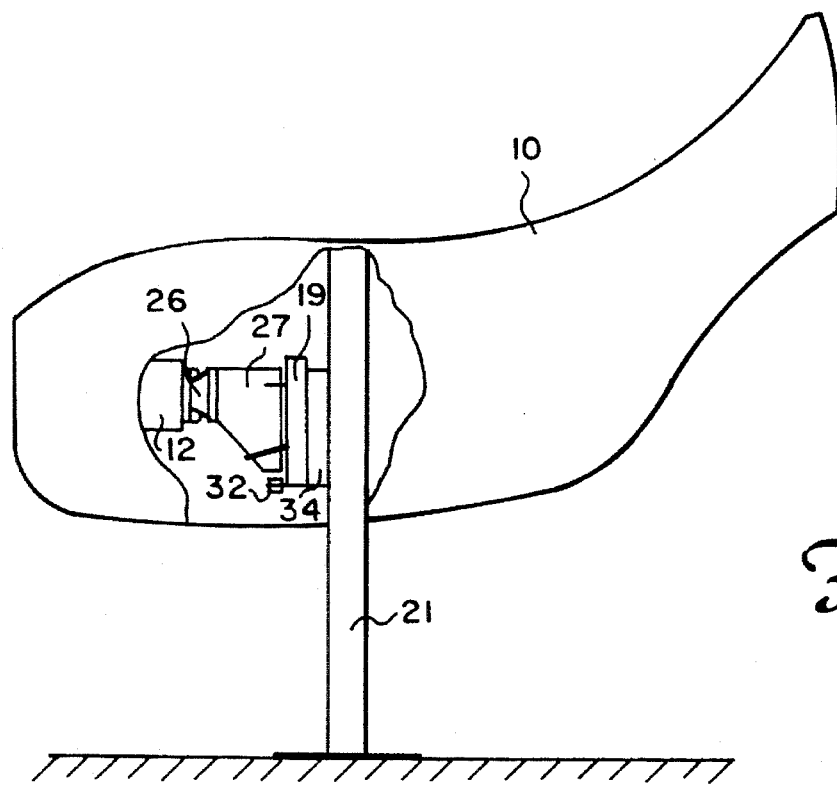
FIG. 3 shows the arrangement of the collecting apparatus according to FIG. 1 inside the dummy horse, as a side view and in partial cross section.

FIG. 3 shows the arrangement of the collecting apparatus according to FIG. 1 inside the dummy horse, as a side view and in partial cross section. Inside the frame 10 of the dummy horse coated with flexible material is installed a collector funnel 27, immediately after the artificial vagina 12, the said funnel being connected to the artificial vagina by means of a protective film 26. The funnel 27, together with its fastening rack and the drive unit 19, is fastened to the frame of the dummy horse 10 by means of a fastening rack 34. The collecting apparatus is easily removable through the open belly part of the dummy horse 10 for cleaning and sterilization.

Figure 4:
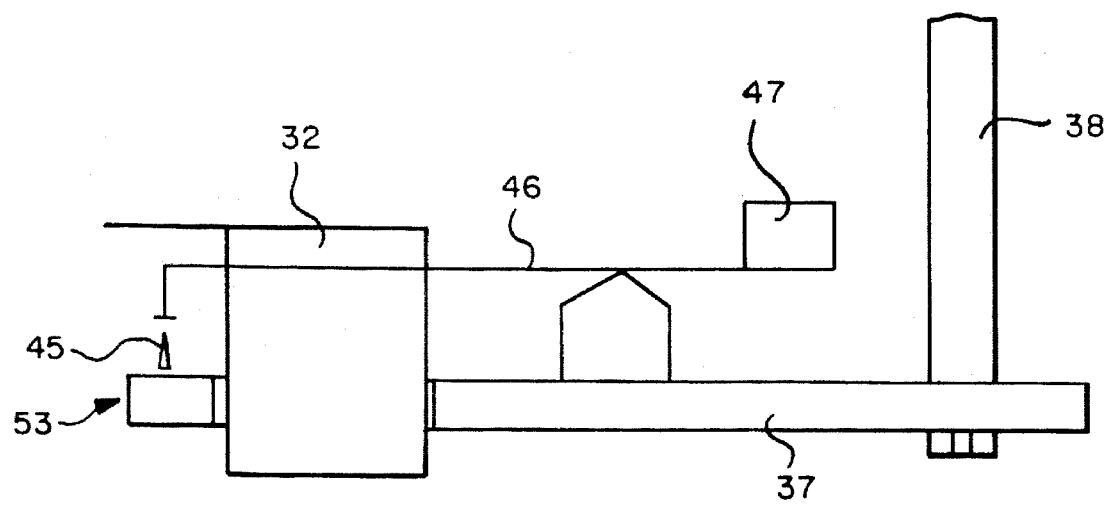
FIG. 4 shows a second embodiment of the receiver weighing system of FIG. 1.

FIG. 4 shows a second embodiment of the receiver 32 weighing system. The measurement of the amount of semen functions in this embodiment on the principle of scales. The weighing elements are adjustable scales fitted to the holder 37 and supporting the receiver 32, there being a sensor 45 between that end 53 of the scales which is on the side of the receiver 32, and the holder, the said sensor being electrically coupled to the transfer device. The weight increase caused by the semen flowing from the collector funnel to the receiver 32 gives the sensor 45 an impulse which causes a transfer motion in the drive unit moving the receiver holder plate 37 through the shaft 38. Each receiver 32 is provided with its own weighing device. The receiver 32 is fastened to one end of the weighing shaft 46, and to the opposite end of the shaft 46 is fastened an adjustable weight 47, by means of which is predetermined the amount of semen to be collected in each receiver 32.

It is obvious to one skilled in the art that the different embodiments of the invention may vary within the scope of the claims presented below.

I claim:

1. A collecting apparatus for collecting semen to be used in animal breeding connected to an artificial vagina, said apparatus comprising:

an artificial vagina;

a plurality of receivers for semen;

a collector funnel connected to said artificial vagina and aligned with a first of said receivers, said funnel comprising an upper semen-receiving opening and a lower discharge opening;

a holder;

a weighing element fitted to said holder for weighing the contents of a said receiver positioned by said holder below the discharge opening of said collector funnel, said weighing element for generating a signal; and wherein a signal generated by said weighing element indicates that an empty receiver can be moved into position in said holder below the discharge opening of said collector funnel once said first receiver has been filled with semen.

2. A collecting apparatus as recited in claim 1 further comprising a frame supporting said apparatus; and wherein said holder comprises a plate and shaft for rotating said plate, said shaft attached to said frame; and wherein said plurality of receivers are connected to said plate spaced a substantially uniform radial distance from said shaft, said uniform radial distance corresponding to the distance from said shaft to said discharge opening.

3. Apparatus as recited in claim 1 wherein said weighing element comprises a measuring device fitted in said holder under said receiver; and further comprising a transfer device electrically coupled to said weighing element to receive a signal from said weighing element.

4. Apparatus as recited in claim 1 wherein said weighing element comprises a plurality of adjustable scales fitted to said holder and supporting a said receiver; a sensor between said scales and said holder; and a transfer device electrically coupled to said sensor.

5. A collecting apparatus for collecting semen from an animal and connected to an artificial vagina, said apparatus comprising:

an artificial vagina;

a collector funnel having an upper opening positioned with respect to said artificial vagina to receive semen from the animal, and a lower discharge opening in communication with the upper opening;

a holder;

at least one semen receiver held in said holder and aligned to receive semen from said discharge opening of said collector funnel; and fitted weighing elements supported by said holder for weighing the contents of said at least one semen receiver when held in position by said holder below said discharge opening.

6. A collecting apparatus as in claim 5 wherein said at least one receiver comprises a plurality of receivers; and wherein said weighing elements further comprise a sensor for detecting that a receiver is filled with semen and for generating a signal that causes said holder to move an empty receiver into alignment with said discharge opening.

7. A collecting apparatus as recited in claim 5 wherein said receiver comprises a plurality of receivers; and wherein said holder further comprises a rotatable plate having receptacles for said plurality of receivers; and further comprising means for incrementally rotating said plate to sequentially move each of said receivers into alignment with said discharge opening.

8. Apparatus as recited in claim 5 wherein said weighing element comprises a measuring device fitted in said holder under said receiver; and further comprising a transfer device electrically coupled to said weighing element to receive a signal from said weighing element.

* * * * *